US006306167B1

(12) United States Patent
Bernau et al.

(10) Patent No.: US 6,306,167 B1
(45) Date of Patent: *Oct. 23, 2001

(54) DEFORMABLE INTRAOCULAR LENS WITH ANCHORED HAPTICS

(75) Inventors: Werner G. Bernau, Koeniz (CH); Thomas J. Chambers, Upland, CA (US)

(73) Assignee: Staar Surgical AG, Nidau (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/289,538

(22) Filed: Apr. 12, 1999

(51) Int. Cl.[7] .................................................. A61F 2/16
(52) U.S. Cl. ..................... 623/6.46; 623/6.47; 623/6.49
(58) Field of Search ................... 623/6.37, 6.42, 623/6.46, 6.47, 6.49, 6.54

(56) References Cited

U.S. PATENT DOCUMENTS

| 4,573,998 | * | 3/1986 | Mazzocco | 623/6.46 |
| 4,786,445 | * | 11/1988 | Portnoy et al. | 264/1.4 |
| 4,834,749 | * | 5/1989 | Orlosky | 623/6.46 |
| 4,834,751 | * | 5/1989 | Knight et al. | 623/6.46 |
| 4,888,013 | * | 12/1989 | Ting et al. | 623/6.46 |
| 5,522,890 | * | 6/1996 | Nakajima et al. | 623/6.46 |

FOREIGN PATENT DOCUMENTS

| 7-23989 | * | 1/1995 | (JP) . |
| 10-14955 | * | 1/1998 | (JP) . |

* cited by examiner

Primary Examiner—Paul B. Prebilic
(74) Attorney, Agent, or Firm—Law Offices of William L. Klima, P.C.

(57) ABSTRACT

A deformable intraocular lens having a resilient haptic portion anchored into a deformable lens portion. Preferably, the haptic portion is anchored in a manner to the lens portion to provide a compressive type of connection therebetween. This anchoring configuration is particularly suitable for use with deformable intraocular lenses made of a collagen-based lens material (e.g. "Collamer").

19 Claims, 6 Drawing Sheets

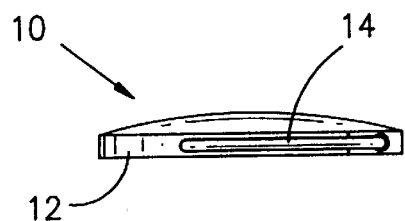
FIG. 4
FIG. 5
FIG. 6
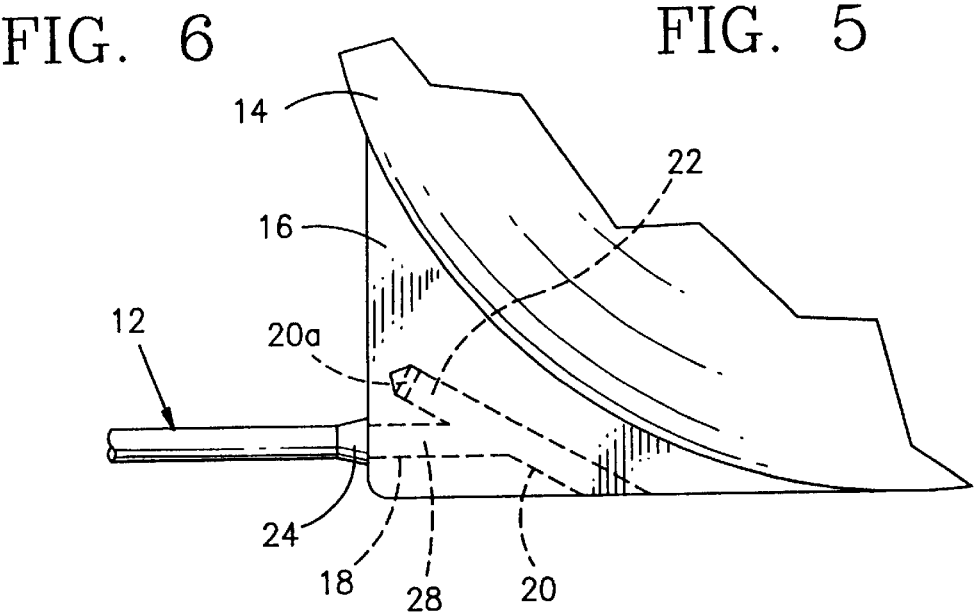
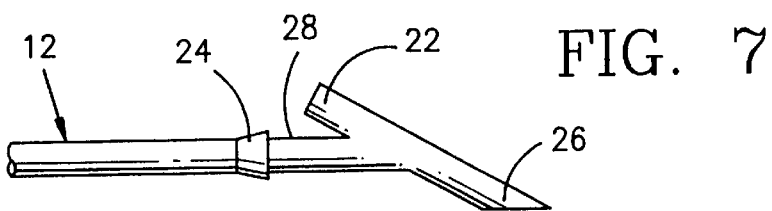
FIG. 7
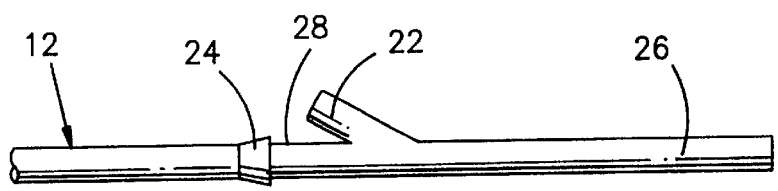
FIG. 8

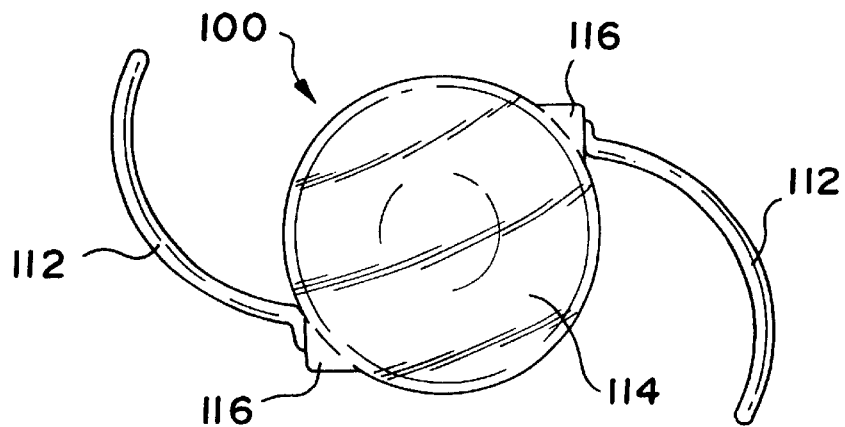
FIG. 16
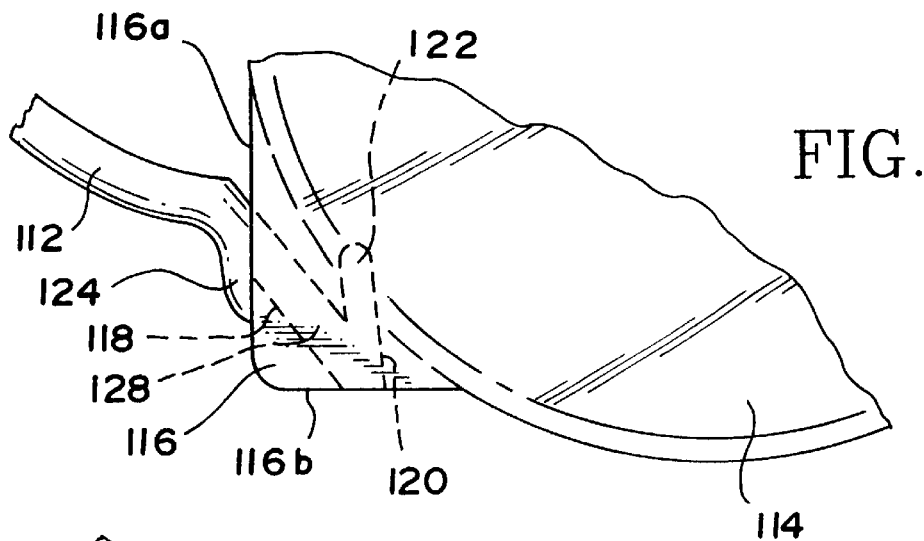
FIG. 17
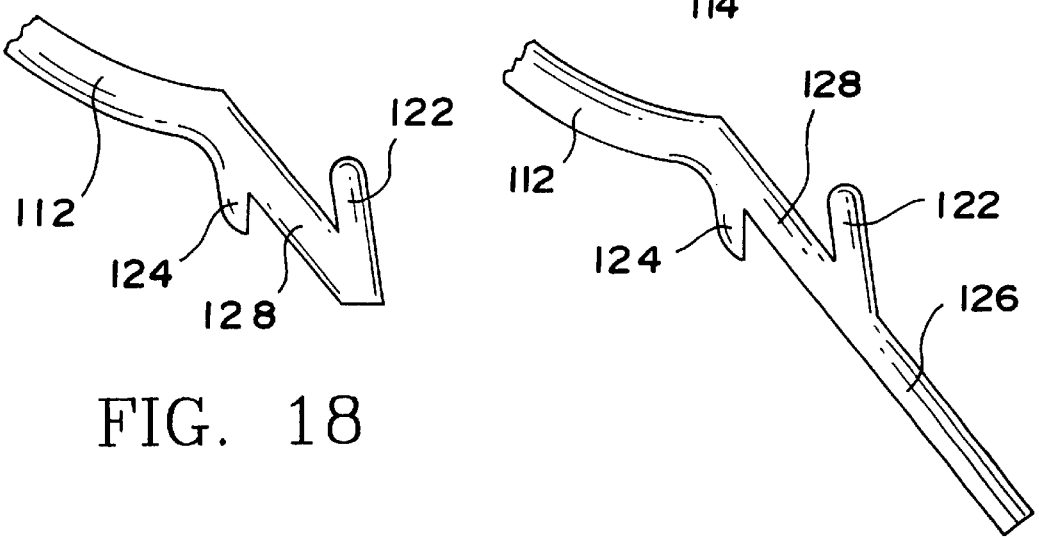
FIG. 18
FIG. 19

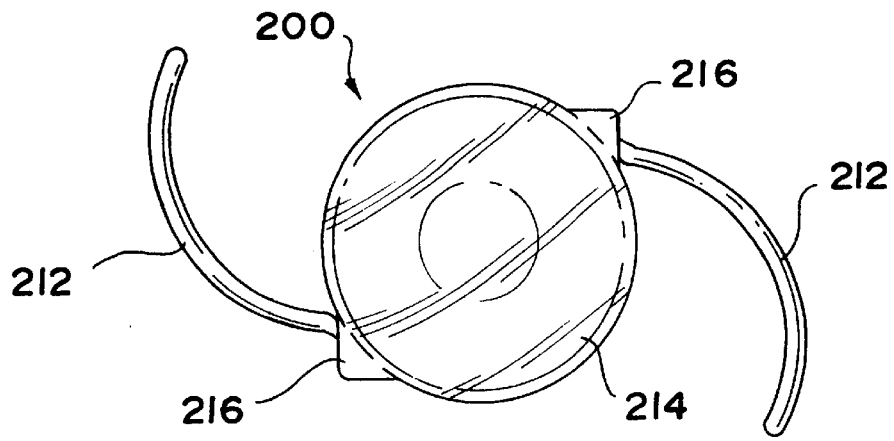
FIG. 20
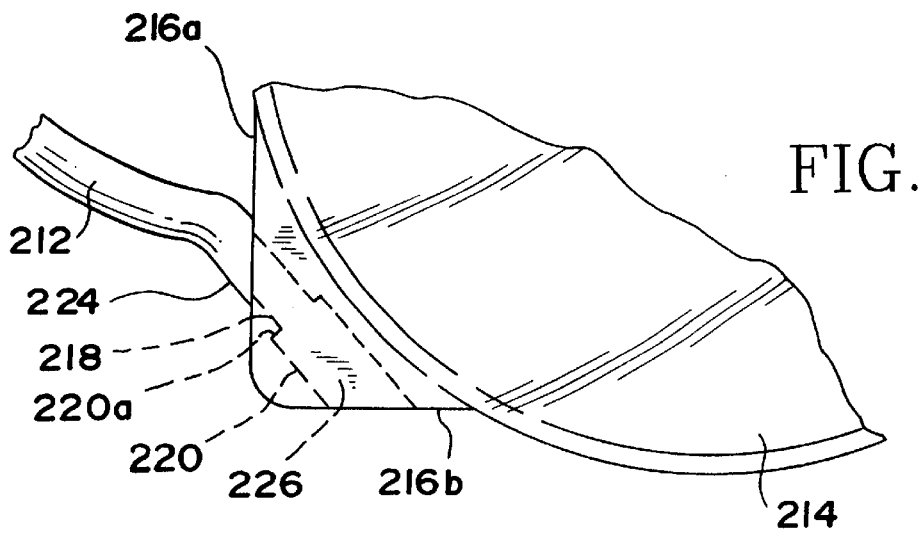
FIG. 21
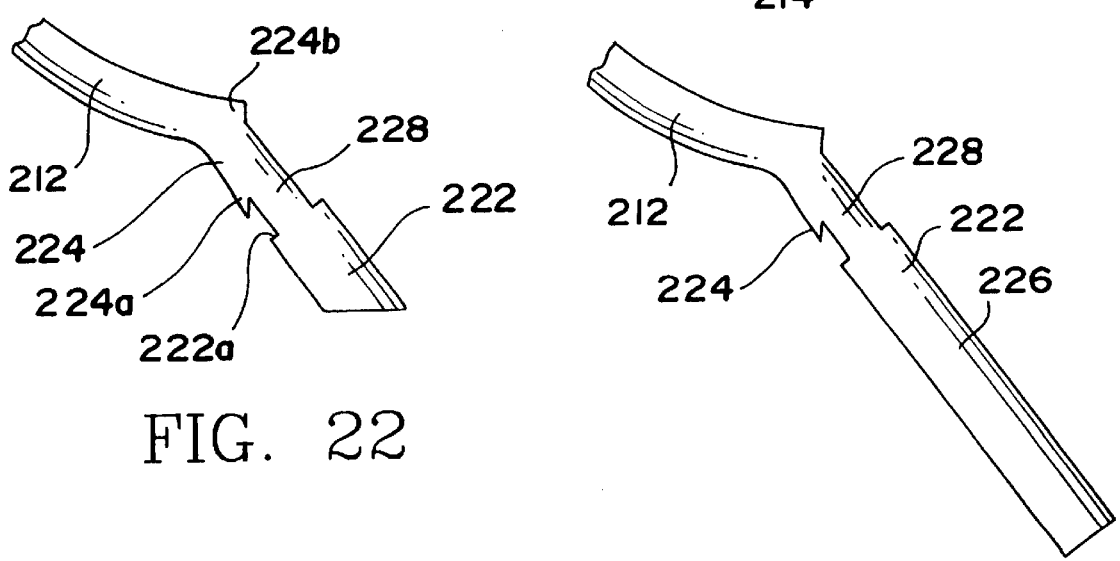
FIG. 22
FIG. 23

DEFORMABLE INTRAOCULAR LENS WITH ANCHORED HAPTICS

FIELD OF THE INVENTION

The present invention is directed to a deformable intraocular lens, and a method of anchoring the deformable intraocular lens.

BACKGROUND OF THE INVENTION

The deformable intraocular lens was invented and developed by Dr. Thomas R. Mazzocco. Dr. Thomas R. Mazzocco with others began Staar Surgical Company of Monrovia, Calif. Today, Staar Surgical Company is one of the leading manufacturers of deformable intraocular lenses in the United States.

Deformable intraocular lenses are made of a variety of material, including silicon, hydrogel and collagen-based materials. Deformable intraocular lenses come in two basic designs, including 1) a three-piece lens (e.g. elastomeric lens manufactured by Staar Surgical Company, Inc.), and 2) a plate-type haptic lens. The present invention is directed to a three-piece type lens. However, the present invention is also applicable to other designs of deformable intraocular lenses having one or more haptic portions anchored into a lens portion. The term "anchored" defines the manner of connection between a connecting end of the haptic portion and the lens portion.

The anchoring of a haptic portion to a lens portion is particularly important with regard to ensuring that the deformable intraocular lens remains assembled during insertion, implantation, and throughout its life in the eye.

The haptic portion of a three-piece type deformable intraocular lens can be made from a variety of biocompatible materials. For example, the haptic portion can be made of polyurethane, polypropylene (e.g PROLENE), polyiimide, polymethylmethacrylate (PMMA), or other biocompatible suitable material. The present invention is particularly suitable with a resilient haptic portion (e.g. made of resilient material such as polyiimide and/or having a resilient design.) The resilient nature of the design and/or material making up the haptic portion is important with respect to securely anchoring a connecting end portion of the haptic portion in the lens portion.

There exists a number of suitable methods for securely anchoring haptics in silicon and hydrogel type deformable intraocular lens. However, securely connecting a haptic portion to a collagen containing polymer material (e.g. Collamer) has been a recent challenge.

SUMMARY OF THE INVENTION

A first object of the present invention is to provide an improved deformable intraocular lens.

A second object of the present invention is to provide an improved connection between a haptic portion and lens portion of a deformable intraocular lens.

A third object of the present invention is to provide an improved connection between a resilient haptic portion and lens portion of a deformable intraocular lens.

A fourth object of the present invention is to provide a deformable intraocular lens including a lens portion having an anchoring hole configured to accommodate and interlock with a connecting end of a haptic portion.

A fifth object of the present invention is to provide a deformable intraocular lens including a resilient haptic portion connected to a resilient lens portion.

A sixth object of the present invention is to provide a deformable intraocular lens including a haptic portion having a connecting end portion connected to a resilient lens portion, the connecting end portion being under resilient tension and a connecting portion of the lens portion being under resilient compression when assembled together.

A seventh object of the present invention is to provide a deformable intraocular lens including a resilient haptic portion connected to a resilient lens portion, the resilient haptic portion including a connecting end portion including a stop portion and barb portion for anchoring the connecting end portion within a hole in the lens portion.

The present invention relates to a deformable intraocular lens. The deformable intraocular lens according to the present invention includes a haptic portion and lens portion. Preferably, both the haptic portion and lens portion are made of resilient materials. For example, the haptic portion can be made of polyurethane, polypropylene, polyiimide, polymethylmethacrylate (PMMA), or other suitable biocompatible material and the lens portion is made of silicone elastomer, hydrogel polymer, collagen containing polymer material (e.g. "Collamer," manufactured by Staar Surgical A.G. of Switzerland), organic or synthetic gel compounds, polyurethane elastomer, or other suitable biocompatible material. The present invention is directed to the configuration of the connection between the haptic portion and lens portion for suitably anchoring the haptic portion to the lens portion.

An important goal of the present invention is to provide a very secure connection between the haptic portion and lens portion of a deformable intraocular lens so that the deformable intraocular lens can be inserted through a small incision in a rolled, folded and/or compressed state, implanted in the eye, and then remain securely assembled together throughout the life of the deformable intraocular lens within the eye. The present invention is particularly suitable with a resilient haptic portion and a resilient lens portion connected together. The present invention is more preferable with a resilient haptic portion and a resilient lens portion made of a collagen containing resilient polymer material such as "Collamer" manufactured by Staar Surgical AG of Switzerland.

An important aspect of the present invention is providing a type of connection between the haptic portion and lens portion that places connection areas of the lens portion under compression (i.e. prestressed). Specifically, the haptic portion is configured to be placed under tension when connected to the lens portion, which in turn places the connection areas of the lens portion under compression. This type of connection provides a very secure and durable type of connection and prevents tearing (i.e. shear) of the material of the lens portion. A particular embodiment utilizes the combination of a stop portion and barb portion for cooperating with a hole made in the lens portion. Specifically, the stop portion is configured to cooperate with an outer surface area surrounding an opening leading into the hole of the lens portion, and the barb portion is configured to cooperate with an indentation in the hole of the lens portion.

The stop portion can take on many different shapes and sizes, and can engage with one or more different outer surface portions at, adjacent, near, or in the vicinity of the entrance or opening into the hole in the lens portion. The stop portion can be entirely external to the lens portion, can be partially located inside the lens portion, or can be configured to be located internal of the lens portion (e.g. hole and concentric countersunk hole). The barb portion is preferably located and configured to be located within the hole in the lens portion, however, can be partially located internal and external, or even completely external at an opposite end of the hole in the lens portion. The barb portion is preferably configured to cooperate with an indentation or catch or stop located within the hole in the lens portion. A preferred indentation is another separate hole drilled at an angle (e.g. preferably reverse angle) relative to the first hole in the lens portion. This configuration allows the barb portion to securely hook into the second hole providing a strong and durable connection between the haptic portion and lens portion.

The hole in the lens portion can be circular, square, rectangular, triangular, oval, pentagon, hexagon, heptagon, octagon, star-shaped or any other suitable shape. The cross-section of the connecting end portion of the haptic portion can have a matching cross-sectional shape to the shape of the hole in the lens portion, or can be different therefrom. The connecting end portion of the haptic portion can be undersized, of equal size, or oversized with respect to the dimensions of the hole in the lens portion. Further, the connecting end portion of the haptic portion can be also adhesively connected, heat welded, ultrasonically welded, fused, or secured in some other manner in addition to mechanical fastening.

In one preferred embodiment, the haptic portions are made from a flat sheet of polyacrylamide material, and made by a chemical etching and masking process. Thus, haptic portions made in this manner, tend to have a square or rectangular cross-sectional shape. The holes in the lens portion can be drilled (i.e. round). The connecting end portions of the haptic portions are designed so that they can be threaded into a hole in the lens portion, and pulled through the hole until the stop portion engages with the lens portion, and continued to be pulled until the barb portion fastens into the other hole portion in the lens portion. The lead end of the haptic portion is then released and cut with a razor blade. The section of haptic portion between the stop portion and barb portion is thus under tension after assembly.

A method of anchoring a deformable intraocular lens according to the present invention includes the following steps: making the haptic portion, making the lens portion, making a hole in the lens portion, and assembling the haptic portion to the lens portion. The step of making the haptic portion preferably includes making both a stop portion and barb portion on a connecting end portion of the haptic portion. The haptic portion can be made from a flat sheet of material, cut or chemically etched to provide a profile shape of the haptic portion made from the sheet material. The lens portion can be molded or machined (e.g. numerical lathe) depending on the material. In the use of "Collamer", a button of material in a dry state is machined with a numerical lathe to provide the prescription profile and connecting flange portions to cooperate with the haptic portions. Two separate holes are drilled from different angles to provide the anchoring hole of the lens portion for each haptic portion. The first hole portion is drilled a predetermined length and then a second hole portion is drilled at an angle relative to the first hole portion and over drilled to extend past a wall of the first hole portion. The hole in the lens portion can be provided by other methods including other machining processes, laser, heat, cutting, etc.

BRIEF DESCRIPTION OF THE DRAWINGS

FIG. 4 is a short side edge view of a deformable intraocular lens shown in FIG. 2.

FIG. 5 is a cross-sectional view of the deformable intraocular lenses indicated in FIG. 2.

FIG. 6 is a detailed broken away top planar view of a connecting portion of the deformable intraocular lens shown in FIG. 2 showing the detail of the anchoring hole configuration.

FIG. 7 is a detailed top planar view of a haptic portion in a configuration when anchored in the connection portion of the lens portion.

FIG. 8 is a detailed top planar view of a connecting end portion of the haptic portion showing the stop and barb, prior to insertion in a hole through a connecting portion of the lens portion.

FIG. 16 is a top planar view of a second embodiment of a deformable intraocular lens according to the present invention.

FIG. 17 is a broken away detailed top planar view of a connecting portion of a lens portion with a haptic portion installed within the connecting portion of the lens portion of the deformable intraocular lens shown in FIG. 16.

FIG. 18 is a broken away top planar view of a portion of the haptic portion in a configuration when installed on the lens portion of the deformable intraocular lens as shown in FIGS. 16 and 17.

FIG. 19 is a broken away detailed top planar view of the connecting portion prior to assembly and trimming.

FIG. 20 is a top planar view of third embodiment of a deformable intraocular lens according to the present invention.

FIG. 21 is a broken away detailed top planar view of a connecting portion of a lens portion with a haptic portion installed within the connecting portion of the lens portion of the deformable intraocular lens shown in FIG. 16.

FIG. 22 is a broken away top planar view of a portion of the haptic portion in a configuration when installed on the lens portion of the deformable intraocular lens as shown in FIGS. 16 and 17.

FIG. 23 is a broken away detailed top planar view of the connecting portion prior to assembly and trimming.

DETAILED DESCRIPTION OF PREFERRED EMBODIMENTS

The characteristics and features of a deformable intraocular lens according to the present invention is shown and described in U.S. Pat. Nos. 4,573,998, 4,702,244, and 5,776, 191 to Dr. Thomas R. Mazzocco, incorporated herein by reference. The deformable intraocular lens according to the present invention is configured to be inserted through a small incision in the eye, preferably under 3 mm, more preferably under 2½ mm, most preferably under 2 mm. The deformable intraocular lenses according to the present invention can be inserted by forceps, or more preferably by a lens injecting device such as taught by U.S. Pat. Nos. 5,312,414, 5,494,484, and 5,499,987 to Vladimir Feingold, incorporated herein by reference.

The present invention is particularly suitable for three-piece type deformable intraocular lenses including a lens portion and two separate loop-type haptic portions anchored into the lens portion. The haptic portions are preferably made of resilient material, for example, polyurethane, polypropylene, polyiimide, polymethylmethacrylate (PMMA), or other suitable biocompatible material. The lens portion is preferably made of a resilient material, including silicone elastomer, hydrogel polymer, collagen containing polymer material (e.g. Collamer), organic or synthetic gel compounds, polyurethane elastomer, or other suitable biocompatible material. A preferred embodiment according to the present invention utilizes haptic portions made from polyimide sheet material in combination with a collagen containing polymer lens material (e.g. "Collamer"). The "Collamer" material is disclosed in detail in U.S. Pat. Nos. 5,654,349, 5,654,363, 5,654,388, and 5,661,218 to Vladir Feingold and Alexi V. Osipov, incorporated herein by reference.

Figure 1:
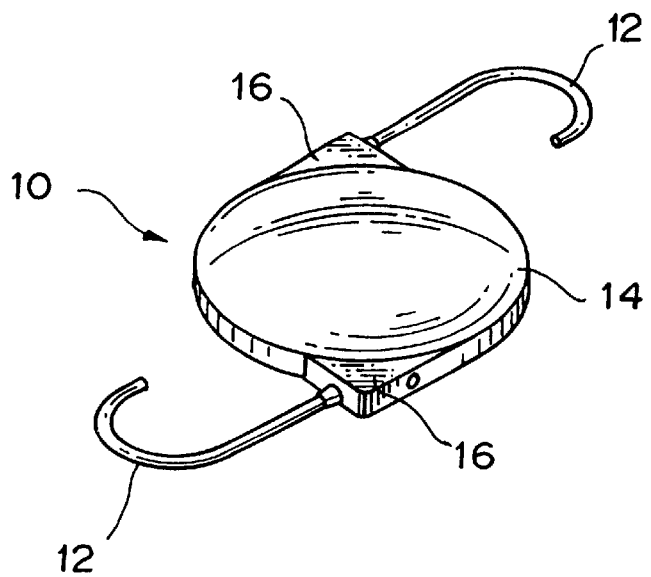
FIG. 1 is a perspective view of a deformable intraocular lens according to the present invention.
Figure 2:
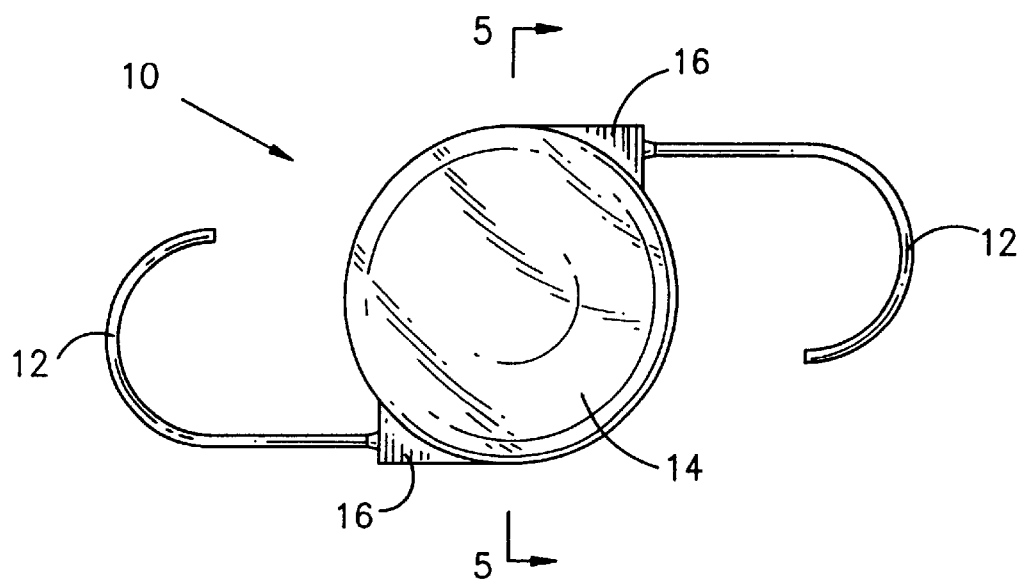
FIG. 2 is a top planar view of the deformable intraocular lens shown in FIG. 1.
Figure 3:
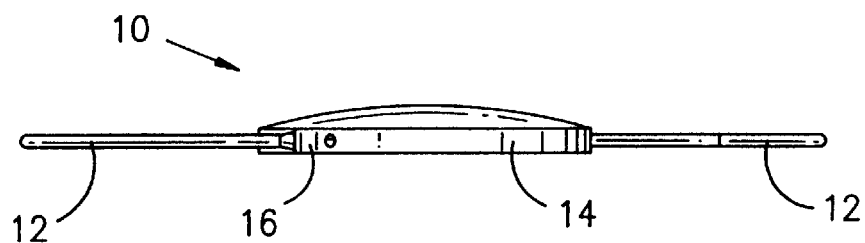
FIG. 3 is a long side edge view of the deformable intraocular lens shown in FIG. 2.

A deformable intraocular lens 10 according to the present invention is shown in FIG. 1. The deformable intraocular lens 10 includes haptic portions 12 and lens portion 14. The haptic portions 12 are anchored in the lens portion 14. The anchoring process is such that the haptic portions 12 remain securely anchored in the lens portion during lens insertion, lens implantation, and throughout the life of the deformable intraocular lens 10 in the eye. The haptic portions 12 can have the shape and profile shown in FIG. 2, however, other shapes and configurations of the haptic portions are possible. Other suitable haptic portions are shown in U.S. Pat. Nos. 4,573,998, 4,702,244, and 5,776,191 to Dr. Thomas R. Mazzocco, incorporated herein by reference.

The deformable intraocular lens can be designed for placement in the anterior chamber and/or posterior chamber (e.g. capsular bag). In addition the deformable intraocular lens can be a phakic refractive lens or "prl" (e.g. "ICL" manufactured by Staar Surgical Company, Inc. of Monrovia, Calif.) The "IOL" can be a conventional "IOL", toric "IOL", multi-focal IOL, etc.

The lens portion 14 is provided with a pair of connecting portions 16. The lens portion 14 with connecting portions 16 can be made by molding (e.g. compression molding) and/or machining in the use of "Collamer" material manufactured by Staar Surgical AG of Switzerland. Specifically, a button of "Collamer" can be machined on numerical lathe to provide the proper lens profile for a prescription, and the connecting portion 16 can also be machined from the same piece of material.

The haptics 12 shown are C-shaped, however, other suitable haptic designs can be substituted for the ones shown. For example, the lens portion can be provided with four connecting portions located at corners of the lens portion and the haptics can be full loops anchored at both ends to a pair of the connecting portions. Alternatively, the haptic can be a ring connected to the lens portion (e.g. by bridging haptic portions).

The connecting portion 16, shown in FIG. 6, is provided with a first hole 18 extending into a second hole 20. Specifically, the second hole 20 is provided at a reversed angle relative to the first hole 18. This configuration provides an indentation 20a for cooperating with a hook or barb portion 22 of the connecting end of the haptic portion 12. The configuration of the connecting end portion of the haptic portion 12 once assembled in the first hole and second hole in the connecting portion 16 of the lens portion, is shown in FIG. 7. The connecting end portion of the haptic portion 12 is also provided with a stop portion 24. The stop portion can be integral with the haptic portion 12, or can be a separate piece. For example, the stop portion 24 can be a length of the haptic portion 12 having an increased diameter. The connecting end portion of the haptic portion 12 prior to assembly with the connecting portion 16 of the lens portion is shown in FIG. 8.

The haptic portion 12 is provided with a removable extension end portion 26 utilized to facilitate assembly with the connecting portion 16 of the lens portion. It is to be noted that the extended end portion 26 is aligned with a haptic portion located on an opposite side of the stop 24 as shown in FIG. 8, prior to assembly and becomes bent adjacent to the barb 22 when assembled, as shown in FIG. 7. The extended end portion 26, is threaded into the first hole 18 of the connecting portion 16 of the lens portion and then exits through the second hole 20 when further inserted. The final assembly involves pulling on the end of the extended end portion 26 and pulling until the barb portion 22 extends past an edge of the first hole 18 so that the barb 22 will engage with the indentation 20 provided by the second hole 20, as shown in FIG. 6.

Method of Anchoring an Intraocular Lens

Figure 9:
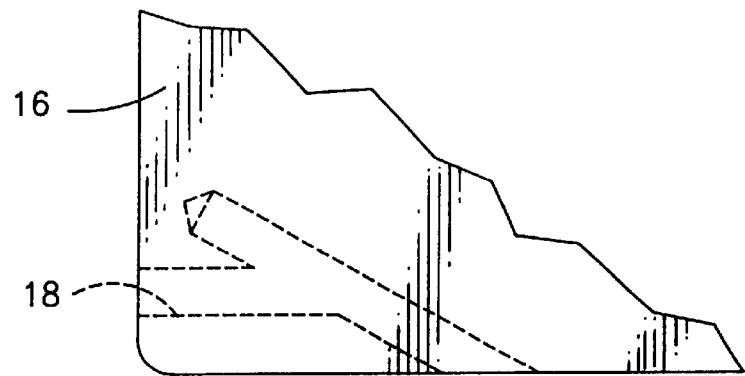
FIG. 9 is a broken away detailed top planar view of a connecting portion of a lens portion showing a first hole drilled in the connection portion.

The connecting portion 16 of the lens portion is provided with a first hole 18, as shown in FIG. 9. In the use of "Collamer" material, the hole 18 is provided by drilling a button of the "Collamer" material in a solid dry state prior to being wetted.

Figure 10:
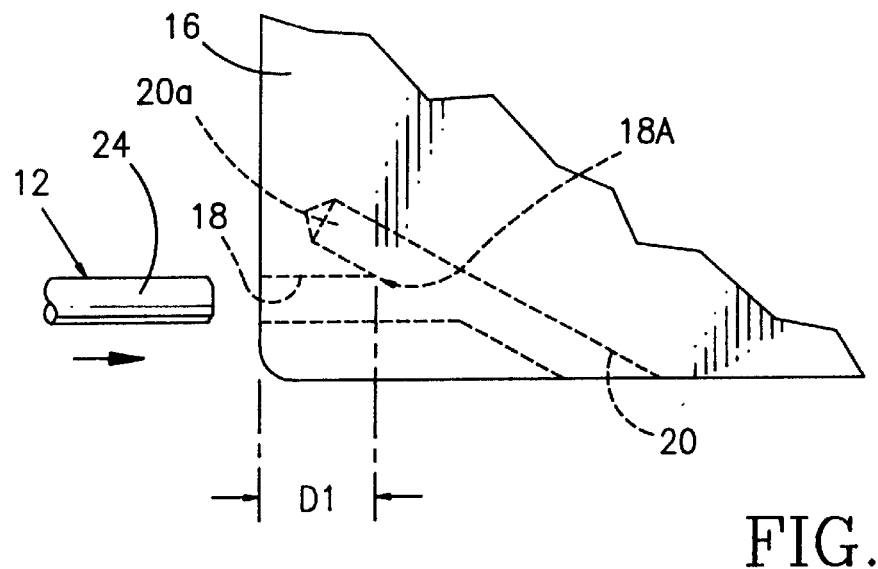
FIG. 10 is a broken away detailed top planar view of the connecting portion of the lens portion shown in FIG. 9. However, with a second hole drilled at a reversed angle relative to the first hole to provide an indentation for cooperating with a barb portion of the haptic portion.

In the next step, a second hole 20 is provided at a reverse angle relative to the first hole 18 as shown in FIG. 10. The second hole 20 can also be drilled in the use of "Collamer" material in its solid dry state. The second hole 20 is purposely drilled at a reverse angle relative to the first hole to provide an indentation 20a having a hook-type configuration to cooperate with a reverse angle barb portion 22 of the haptic portion 12.

Once the first hole 18 and second hole 20 are provided, the removable extended end portion 26 of the haptic portion 12 is threaded into an opening of the first hole 18, as shown in FIG. 10. The extended end portion 26 is threaded all the way into the first hole 18 until it contacts with an inclined wall of the second hole 20. The haptic portion 12 is further forced into the connecting portion 16 so that the extended end portion 26 bends and exits out of the second hole 20, as shown in FIG. 12.

Figure 12:
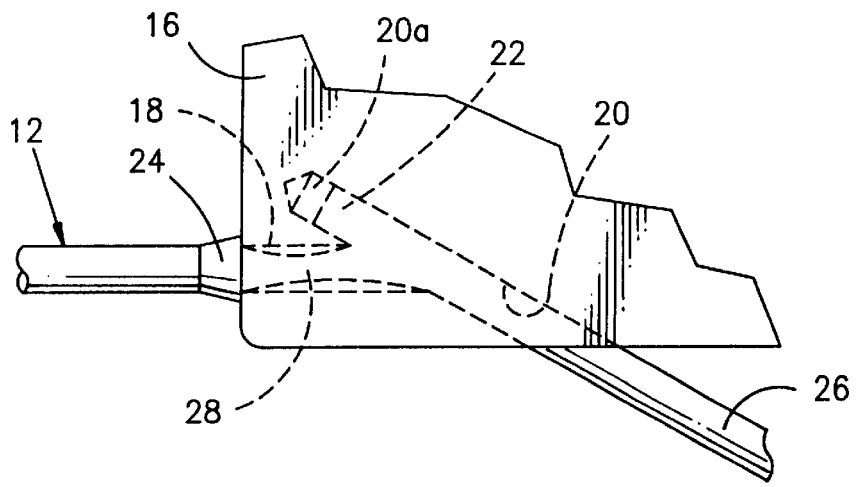
FIG. 12 is a broken away detailed top planar view of a connecting portion of a lens portion with a haptic portion installed within the connecting portion of the lens portion just after assembly and prior to trimming a very end portion of the haptic portion.
Figure 13:
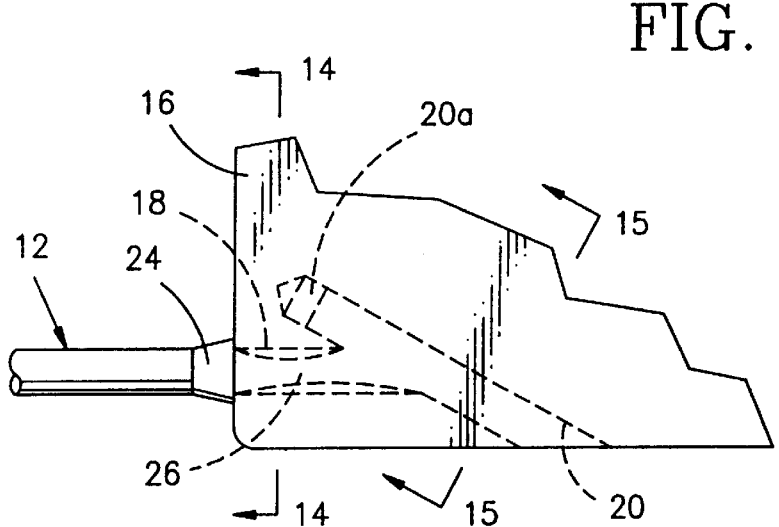
FIG. 13 is a broken away detailed top planar view of the configuration shown in FIG. 12, however, after trimming an end portion of the haptic portion.

The extended end portion 26 is pulled so as to stretch a mid-portion 28 of the haptic portion 12 located between the barb portion 22 and stop portion 24, as shown in FIG. 12. The extended end portion 26 is pulled so that the barb 22 extends past an end edge 18a (FIG. 10) of the first hole 18, and then released so that the barb portion 22 backs into the indentation 20a of the second hole 20. In this manner, the barb 22 becomes hooked into the reverse angle indentation 20a.

As shown in FIG. 20, when the haptic portion 12 is assembled to the connecting portion 16 of the lens portion, the mid-portion 28 is under tension due to the resilience and elastic property of the material of the haptic portion 12. The tensile force exerted on the mid-portion 28 by stretching creates an equal and opposite force on the barb portion 22 and stop portion 24 causing compression of zones of the connecting portion 16 located between the barb portion 22 and stop portion 24 and adjacent the first hole 18. This compressive type of connection provides an extremely strong type of connection capable of enduring forces exerted on the deformable intraocular lens on being inserted through a small incision, implanting the lens in the eye, and throughout the life of the deformable intraocular lens within the eye.

Figure 14:
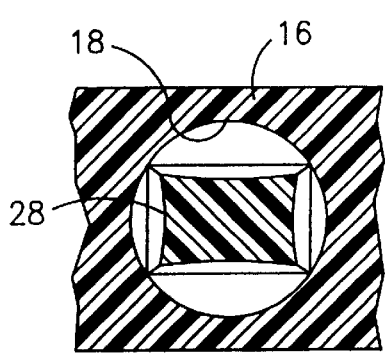
FIG. 14 is a detailed lens thickness cross-sectional view as indicated in FIG. 13.
Figure 15:
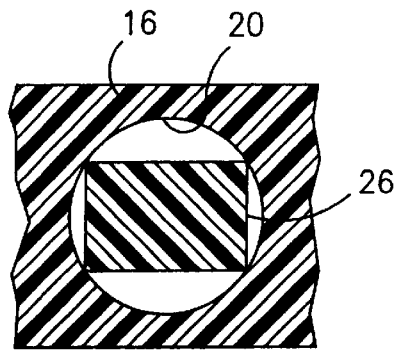
FIG. 15 is a detailed lens thickness cross-sectional view as indicated in FIG. 13.

FIG. 14 shows a reduction in the cross-sectional dimensions of the mid-portion 28 of the haptic portion 12 due to it being placed under tension. In contrast, a portion of the haptic portion 12 located in the second hole 20 as indicated in 13 is under a neutral load (i.e. no tension or compression) as shown in FIG. 15.

Figure 11:
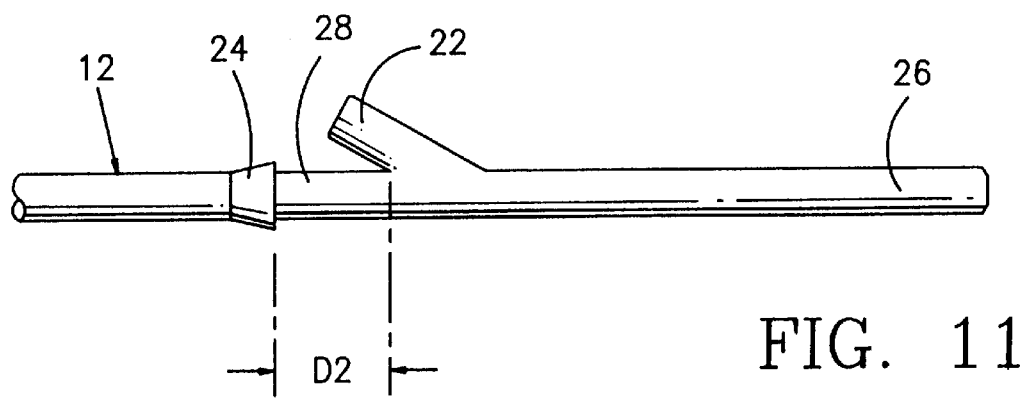
FIG. 11 is a top planar view of a portion of the haptic portion prior to assembly showing the stop portion and barb portion.

The haptic portion 12 and the connecting portion 16 of the lens portion 14 are configured to provide for a compressive type connection. In the embodiment shown, a minimum length dimension of the first hole 18 is indicated as D1, as shown in FIG. 10. The first hole 18 has a minimum length dimension and a maximum length dimension, since a right end of the first hole 18 is angled due to the orientation of the second hole 20. The length of the mid-portion 28 of the haptic portion 12 is shown in FIG. 11 as D2. In the compressive type of connection, the dimension D2 is selected to be less than the dimension D1.

Alternatively, the connection can be a neutral (i.e. load D1 is equal to D2), or even D2 can be greater than D1 to purposely provide play in the connection between the haptic portion 12 and connecting portion 16. However, preferably D2 is less than D1 to provide a compressive type of connection between the haptic portion 12 and lens portion 14.

Additional Embodiments

A second embodiment of a deformable intraocular lens 100 according to the present invention as shown in FIGS. 16–19.

The deformable intraocular lens 100 includes haptic portions 112 and lens portion 114. The haptic portions 112 are anchored in the lens portion 114. The anchoring process is such that the haptic portions 12 remain securely anchored in the lens portion during lens insertion, lens implantation, and throughout the life of the deformable intraocular lens 100 in the eye.

The lens portion 114 is provided with a pair of connecting portions 116. The lens portion 114 with connecting portions 116 can be made by molding and/or machining in the use of "Collamer" material manufactured by Staar Surgical AG of Switzerland. Specifically, a button of "Collamer" can be machined on a numerical lathe to provide the proper lens profile for a prescription, and the connecting portions 116 can also be machined from the same piece of material.

The connecting portion 116, shown in FIG. 17, is provided with a first hole 118 extending into a second hole 120. Specifically, the second hole 120 is provided at a reversed angle relative to the first hole 118. This configuration provides an indentation for cooperating with a barb portion 122 of the connecting end of the haptic portion 112. The configuration of the connecting end portion of the haptic portion 112 once assembled in the first hole and second hole in the connecting portion 116 of the lens portion, is shown in FIG. 17. The connecting end portion of the haptic portion 112 is also provided with a stop portion 124. The stop portion can be integral with the haptic portion 112, or can be a separate piece. In the embodiment shown in FIG. 17, the haptic portions 112 are made from a flat sheet of material (e.g. polyiimide) and are cut or etched from the flat sheet of material. Thus, the barb portion 122 and stop portion 124 are essentially two-dimensional projections cut or etched from the flat sheet of material.

The haptic portion 112 is provided with a removable extension end portion 126, as shown in FIG. 19, utilized to facilitate assembly with a connecting portion 116 of the lens portion 114. The extended end portion 126 is threaded into the first hole 118 of the connecting portion 116 and then exits out an end of the first hole 118 when further inserted. The final assembly involves pulling on the end of the extended end portion 126 until the barb portion 122 extends past an edge of the first hole 118 so that the barb portion 122 will engage with the indentation provided by the second hole 120, shown in FIG. 17.

In the embodiment shown in FIG. 17, the hole 118 is set at an angle relative to an edge surface 116a of the connecting portion 116. Further, the first hole 118 is also set at an angle with respect to an edge 116b of the connecting portion 116. The edges 116a and 116b are set at approximately a 90° angle relative to each other. This differs from the embodiment shown in FIG. 6 where the first hole 118 is set approximately perpendicular with respect to a first edge of the connecting portion 116. Furthermore, the first hole 118 extends all the way through the connecting portion 116a in the embodiment shown in FIG. 17 as opposed to only partially extending into the connecting portion 16 in the embodiment shown in FIG. 6.

A further feature of the embodiment shown in FIGS. 16–19 is that the second hole 120 extends towards the lens portion 114. Preferably, the second hole 120 actually extends into the lens portion 114 to provide a stronger connection, since the lens portion 114 begin to widen from the outer peripheral edge towards the center thereof Another feature is that the stop portion 124 is set at a reverse angle relative to the first hole 118 and provides a Z-shaped connecting end when viewing the barb portion 122, stop portion 124 and mid-portion 128, as shown in FIG. 18. This Z-shaped connecting end configuration securely fastens the haptic portion 112, and prevents movement in either direction. Further, the length of the mid-portion 128 is preferably selected to be slightly less than the length of the first hole 118 to provide a compressive connection with the connecting portion 116 once assembled. Once assembled, the connecting portion 116 is in a resilient tensile prestressed condition providing excellent anchoring qualities.

In the second embodiment shown in FIGS. 16–19, the deformable intraocular lens 100 can be assembled by threading the extended end portion 126 into the first hole 118 until the extended end portion 126 exits the first hole 118. The extended end portion 126 is gripped and pulled so that the stop portion 124 engages with the edge portion 116a of the connecting portion 116. The extended end portion 126 is further puffed so that the barb portion 122 extends past an edge of the first hole 118. The extended end portion 126 is then released to allow the barb portion 122 to enter into the second hole 120 and positively lock therein.

Alternatively, an opposite end of the haptic portion 112 (i.e. free end) isthreaded in an opposite direction through the first hole 118 and pulled so that the stop portion 124 is pulled through the first hole 118. The free end of the haptic portion 112 is further pulled until the stop portion 124 exits from the first hole and grips on the outer edge 116a of the connecting portion 116 while the barb portion 122 enters into the second hole 120 and becomes positively locked therein. Thus, the haptic portion 112 can be assembled to the connecting portion 116 from either direction in the embodiment shown in FIGS. 16–19.

A third embodiment of a deformable intraocular lens 200 is shown in FIGS. 20–23.

The deformable intraocular lens 200 includes haptic portions 212 and lens portion 214. The haptic portions 212 are anchored in the lens portion 214. The anchoring process is such that the haptic portions 212 remain securely anchored in the lens portion during lens insertion, lens implantation, and throughout the life of the deformable intraocular lens 200 in the eye.

The lens portion 214 is provided with a pair of connecting portions 216. The lens portion 214 with connecting portions 216 can be made by molding and/or machining in the use of "Collamer" material manufactured by Staar Surgical AG in Switzerland. Specifically a button of "Collamer" can be machined on a numerical lathe to provide the proper lens profile for a prescription, and the connecting portions 216 can also be machined from the same piece of material.

The connecting portion 216, shown in FIG. 21, is provided with a first hole 118 extending into a second hole 220. The second hole 220 has a greater diameter relative to the first hole 218. The first hole 218 is aligned with the second hole 220. This configuration provides an indentation or inner reverse stop 220a for cooperating with a barb portion 222 of the connecting end of the haptic portion 212. The configuration of the connecting end portion of the haptic portion 212 once assembled in the first hole 218 and second hole 220 in the connecting portion 216 of the lens 200, shown in FIG. 21. The connecting end portion of the haptic portion 212 is also provided with a stop portion 224. The stop portion 224 includes a first stop portion protrusion 224a and second stop portion protrusion 224b. Both of these protrusions 224a and 224b cooperate and engage with an edge 216a of the connecting portion 216, shown in FIG. 21.

During assembly, a free end of the haptic portion 212 is threaded into the second hole 220 and then forced into the first hole 218. Once the free end of the haptic portion 212 exits the first hole 218, the free end of the haptic portion 212 is pulled all the way through the first hole 218 and 220. The free end of the haptic portion 212 is pulled until an edge 222a of the barb portion 222 engages with the inner edge 220a of the second hole 220. The free end of the haptic portion 212 is further pulled until the stop portion protrusions 224a and 224b exit out the first hole 218 and engage with the outer edge 216a of the connecting portion 216. The haptic portion 212 is provided with an extended end portion 226, as shown in FIG. 23 prior to assembly. After assembly, the remaining portion of the extended end portion 226 extending out of the second hole 220 is trimmed flush with the outer edge 216b of the connecting portion 216 to have the configuration shown in FIG. 222. Thus, the third embodiment of the deformable intraocular lens 200 according to the present invention is assembled by threading the haptic portion in a reverse direction versus the assembly of the haptic portion in the first embodiment of the deformable intraocular lens 10 shown in FIGS. 1–15.

The mid portion 228 is preferably shorter in length relative to the first hole 218 to provide a compressive type of connection between the haptic portion 212 and the connecting portion 216. Once assembled, the connecting end of the haptic portion 216 is in a resilient tensile pre-stressed condition. Specifically, the mid portion 228 is under resilient tension while a portion of the connecting portion 216 surrounding the hole 218 is under resilient compression. This arrangement provides a very secure connection therebetween.

What is claimed is:

1. A deformable intraocular lens, comprising:
    a deformable lens portion including at least one connecting portion, said connecting portion provided with an anchoring hole extending through said connecting portion; and
    at least one resilient haptic portion, said resilient haptic portion connected to said deformable lens portion, said resilient haptic portion being provided with a connecting end portion including a barb portion and a stop portion, said stop portion located adjacent to an outer opening into said anchoring hole and configured for cooperating and stopping with an outer edge located adjacent to said opening into said anchoring hole and said barb portion configured for cooperating and anchoring with an indentation located within said anchoring hole, said connecting end portion being configured to allow said haptic portion to be assembled into said anchoring hole by threading said haptic portion in at least one direction through said anchoring hole.

2. A lens according to claim 1, wherein a mid-portion of said connecting end of said resilient haptic portion located between said stop portion and said barb portion is under resilient tension when said resilient haptic portion is assembled to said lens portion.

3. A lens according to claim 1, wherein said indentation in said anchoring hole is an indentation hole.

4. A lens according to claim 3, wherein said indentation hole is angled relative to said anchoring hole.

5. A lens according to claim 4, wherein said indentation hole is oriented at a reverse angle and substantially at a same or similar angle as said barb portion relative to said connection end of said resilient haptic portion.

6. A lens according to claim 1, wherein said anchoring hole further comprises two separate connecting holes oriented at an angle.

7. A lens according to claim 6, wherein said anchoring hole further includes a first hole extending into a second hole, said second hole being oriented at an angle relative to said first hole.

8. A lens according to claim 7, wherein said second hole is set at a reverse angle relative to said first hole.

9. A lens according to claim 1, wherein a distance D2 defined between said stop portion and barb portion of said haptic portion is selected to be less than a distance D1 defined by a minimum length dimension of a first hole of said anchoring hole.

10. A lens according to claim 1, wherein said stop portion is defined by a length of haptic portion having an increased outer dimension.

11. A lens according to claim 1, wherein said connecting end portion is configured to allow said haptic portion to be assembled into said anchoring hole by threading said haptic portion in either direction through said anchoring hole.

12. A lens according to claim 1, wherein said anchoring hole includes a first hole portion extending into and aligned with a second hole portion, and said second hole portion having a greater diameter relative to said first hole portion.

13. A lens according to claim 12, wherein said barb portion is configured to be disposed within said second hole portion, and an outer edge of said barb cooperates and engages with an inner edge defined between said first hole portion and said second hole portion.

14. A lens according to claim 1, wherein said anchoring hole is set substantially perpendicular relative to an edge of said connecting portion.

15. A lens according to claim 1, wherein said anchoring hole is set at an angle relative to an edge of said connecting portion.

16. A lens according to claim 15, wherein said anchoring hole extends through said connecting portion and includes a pair of openings in a pair of edges of said connecting portion.

17. A lens according to claim 16, wherein said pair of edges are set at approximately ninety degrees (90°) relative to each other.

18. A lens according to claim 7, wherein said second hole extends into said lens portion.

19. A lens according to claim 12, wherein said second hole extends into said lens portion.

* * * * *